United States Patent [19]

Yasuo et al.

[11] Patent Number: 5,570,181
[45] Date of Patent: Oct. 29, 1996

[54] METHOD OF DETECTING IMPURITIES IN MOLTEN RESIN UTILIZING SCATTERING LIGHT AND THE SHADOWS OF THE IMPURITIES

[75] Inventors: Hiroyuki Yasuo; Hiroshige Deguchi, both of Osaka, Japan

[73] Assignee: Sumitomo Electric Industries Ltd., Osaka, Japan

[21] Appl. No.: 471,443

[22] Filed: Jun. 6, 1995

Related U.S. Application Data

[63] Continuation of Ser. No. 157,327, Nov. 26, 1993, abandoned.

[30] Foreign Application Priority Data

Nov. 25, 1992 [JP] Japan ..................... 4-339776
Sep. 13, 1993 [JP] Japan ..................... 5-252250

[51] Int. Cl.$^6$ .......................... G01N 15/02; G01N 21/00; G01B 11/14; G02B 7/04
[52] U.S. Cl. .......................... 356/336; 356/338; 356/343; 356/375; 356/237; 250/201.2; 250/201.4
[58] Field of Search .......................... 356/335, 336, 356/338, 339, 343, 237, 375, 427, 441, 442; 250/201.2, 201.4

[56] References Cited

U.S. PATENT DOCUMENTS

| | | | |
|---|---|---|---|
| 3,591,290 | 7/1971 | Zinner et al. | 356/335 |
| 3,830,969 | 8/1974 | Hofstein | 356/335 |
| 4,135,821 | 1/1979 | Pechin et al. | 356/335 |
| 4,260,258 | 4/1981 | Rose et al. | 356/335 |
| 4,497,576 | 2/1985 | Caussignac et al. | 356/335 |
| 4,596,036 | 6/1986 | Norgren et al. | 356/336 |
| 4,613,938 | 9/1986 | Hansen et al. | 356/338 |
| 4,969,745 | 11/1990 | Ibe | 356/375 |
| 4,999,513 | 3/1991 | Ito et al. | 356/442 |
| 5,379,113 | 1/1995 | Niwa | 356/336 |

FOREIGN PATENT DOCUMENTS

| | | |
|---|---|---|
| 1292877 | 6/1961 | Germany. |
| 3118453 | 5/1991 | Japan. |
| WO91/08467 | 6/1991 | WIPO. |

*Primary Examiner*—Frank Gonzalez
*Assistant Examiner*—Jason D. Eisenberg
*Attorney, Agent, or Firm*—Wenderoth, Lind & Ponack

[57] ABSTRACT

A method of detecting impurities in a molten resin. The molten resin is massed through a passage having a window through which light can pass. Light is emitted from a light source through the window and the molten resin flowing through the passage. Sensors are used to sense a shadow produced when the light from the light source is interrupted by an impurity contained in the molten resin. Finally, the size of the impurity is measured from the width of the shadow and the intensity of light of the shadow. Also, judgment is made that if optical signals obtained by detecting the light that has passed through the molten resin indicate that there exist bright areas around a dark area, the dark area is distinguished as a shadow of an impurity. Further, in order to judge the shape of an impurity with high accuracy and record its image, a plurality of the devices used in the above method or the device used in the above method and a conventional camera may be used in combination.

7 Claims, 7 Drawing Sheets

METHOD OF DETECTING IMPURITIES IN MOLTEN RESIN UTILIZING SCATTERING LIGHT AND THE SHADOWS OF THE IMPURITIES

This application is a Continuation of now abandoned application, Ser. No. 08/157,327, filed on Nov. 26, 1993.

BACKGROUND OF THE INVENTION

The present invention relates to a method of detecting and distinguish impurities (e.g. metal materials, fibers, voids and ambers) in molten resin by passing light from a light source through the molten resin such as molten polyethylene.

When extruding an insulating coating of a polyethylene on a power cable or forming an extrusion-molded joint of polyethylene at joint portions of the cable, the cable may suffer electrical troubles such as electrical breakdown if the polyethylene contains impurities. Thus, it is necessary to inspect the molten polyethylene to measure the number and size of the impurities.

Also, since such molten polyethylene contains a crosslinking agent, if the temperature of the molten polyethylene is not kept uniform, a runaway crosslinking reaction, known as "ambers", may occur. Thus, the detection and measurement of impurities has to be carried out without changing the temperature and flow rate of the molten polyethylene.

FIG. 6 shows one conventional method of detecting impurities in a molten polyethylene. As shown in the figure, a pipe through which molten polyethylene 32 flows is partially formed as a glass pipe 31. A laser beam is emitted from a light source 33. If there exist impurities in the polyethylene, the laser beam is scattered by them. Thus, by catching the scattered light, one can detect that there are impurities and measure their size.

The arrangement of this figure includes a reflecting mirror 34, a lens 35, a light detector 36 and an oscillograph 37.

With this conventional method, it is possible to detect very small impurities on the order of several micrometers with high sensitivity. But this method has one drawback in that the diameter of the impurities cannot be measured with a high accuracy or cannot be measured at all if the impurities have diameters substantially larger than the wavelength of the laser beam (say, several tens of micrometers) because the strength and direction of scattered light vary according to the shape and surface condition of the impurities.

FIG. 7 shows another conventional method for detecting impurities in a molten polyethylene. As shown in the figure, a glass pipe 41 is in the shape of a sheet and is located within the focal depth of a CCD camera 43. The images of impurities in a molten polyethylene 42 that pass through the pipe are picked up in the form of camera images to detect their shades.

In this method, if it is desired to detect minute impurities, it is necessary to use a lens having a long focal distance. A high magnification means a shallow (short) focal depth. Thus, the passage through which molten polyethylene flows has to be sufficiently wide and thin. The polyethylene is thus more likely to suffer from excessive crosslinking reaction, that is, "ambers".

Further, since the molten polyethylene flows through such a passage at a high speed, image processing has to be carried out at an extremely high speed in order to inspect all of the polyethylene. Moreover, since a glass pipe large enough to cover the entire field of view of the camera is needed, it is necessary to heat the pipe to keep the temperature of the molten polyethylene constant.

SUMMARY OF THE INVENTION

An object of the present invention is to provide a method of detecting impurities in a molten polyethylene which has a wide field of view, a high three-dimensional resolution and a large depth of field.

According to the present invention, there is provided a method of detecting impurities in a molten resin comprising the steps of, passing the molten resin through a passage having a window through which light can pass; emitting light from a light source through the window and the molten resin flowing through the passage; sensing, by means of sensors, shadows produced when the light from the light source is interrupted by an impurity contained in the molten resin, and measuring the size of the impurity from the width of the shadow and the intensity of light of the shadow.

A glass pipe is provided in a passage for molten polyethylene. A light source and a line sensor is provided on opposite sides of the glass pipe so as to be oppose to each other. The intensity of light received by each pixel of the line sensor is monitored.

If there is an impurity in the molten polyethylene, the light from the light source will be interrupted by the impurities. There is a correlation between the amount of light interrupted and the size of the impurities. Also, the greater the distance between the sensor and the impurities, the more markedly the shadow of the impurities tends to be blurred (its intensity weakens) due to the interference of light and the wider its shadows. Thus, the product of the intensity of the shadow and its width is not dependent upon the distance between the impurities and the sensor any more.

Also, it is possible to detect the position of impurities by checking the pixels of the line sensor that indicate a shadow. The detecting accuracy of the position of the impurities and the measurement accuracy of the shadow width are determined by the number and size of pixels in the line sensor. A line sensor having 5000 10 µm pixels is easily available.

How much resolution, field of view and focal distance are attainable with the detecting method of the present invention was examined by the arrangement shown in FIG. 3A. The arrangement comprises an LED light source 21 having a wavelength of 850 nm, a PCF optical fiber 22 having a core diameter of 250 µm, a collimator lens 23, a CCD line sensor 26, a CCD driving circuit 27, a computer 28 and a printer 29. A specimen 24 has four kinds of metal wires, 25a, 25b, 25c and 25d, having diameters of 130 µm, 70 µm, 20 µm and 455 µm, respectively, and is arranged as shown in FIG. 3B. The specimen 24 was moved between points A and B along the optical path as shown in FIG. 3A to see how much detection accuracy of the diameter of impurities changes with the focal depth.

The signal outputs of the CCD are picked up on the pixels of the CCD line sensor, corresponding to the position of the metal wires as shown in FIG. 4A (2048 pixels, field of view: about 28.6 mm, distance between the CCD line sensor and the specimen: about 10 mm). The results are shown in FIG. 5.

As shown in FIG. 5, in the region where the width of the metal wire is about 150 µm or less, linearity is lost between the width and depth (intensity of light) of the shadow and the width of the metal wire due to the diffraction of light. But the product of the width and depth of the shadow for a 455 µm metal wire maintains a good linearity over the entire region. Further, it was found out that this linearity is maintained when the specimen 25 is moved between points A and B, which are 10 mm and 40 mm apart from the line sensor, respectively.

When the method of the present invention is applied to the detection of impurities in a molten polyethylene, the light that has passed through the molten polyethylene is influenced by irregularity (distribution) in the refraction factor due to variations in temperature, flow rate and composition of the molten polyethylene. Thus, it is necessary to distinguish between irregularity in the intensity of light due to the irregular refraction factor and the real shadow of an impurity.

Another object of the present invention is to provide a method of detecting impurities in a molten resin which is capable of distinguishing between irregular refraction factors and the real shadow of an impurity and thus eliminates the possibility of erroneous detection due to a light disturbance resulting from the irregular refraction factors.

According to the present invention, only if the optical signals obtained by detecting the light that has passed through the molten resin indicate that there exist bright areas around a dark area, they are distinguished as shadows of an impurity.

In order to distinguish between a dark region in the optical signals that reflects the real shadow of an impurity and a dark region created by the disturbance of light due to the irregular refraction factors in polyethylene, the following phenomena are utilized in the present invention. Namely, by using a light source such as an LED or a light bulb provided at a sufficient distance from a target area or a moderately coherent light source as shown in FIG. 1, bright portions 2 are created at both ends of a shadow 3 of an impurity due to light diffraction.

The bright portions 2 are in close proximity to both ends of the shadow 3 and their widths and brightness are limited within certain ranges. Thus, by judging whether there are such bright portions around the dark portion, it is possible to distinguish between a dark area due to disturbance of an optical signal 1 resulting from the irregular refraction factors in polyethylene and a dark area that reflects the real shadow of an impurity.

FIGS. 2A–2C show the steps followed in the method of distinguishing impurities in a molten resin according to the present invention. FIG. 2A shows change in the amount of the optical signals obtained by passing light from the light source through the molten resin. FIG. 2B shows the outputs of a comparator for dark-level comparison of the optical signals. FIG. 2C shows the outputs of a comparator for bright-level comparison.

The light source has to have such a coherence that bright portions 2 will appear due to diffraction at both ends of the shadow 3 of an impurity in a molten resin such as molten polyethylene. The optical signals 1 obtained by passing light through the molten resin are binarized by passing them through a comparator having a threshold for a dark-level of the amount of light. If the signals thus binarized indicate any dark area for a predetermined continuous length, this area is picked out as a potential shadow 3' of an impurity.

The optical signals 1 obtained are further binarized by passing them through a comparator having a threshold for a bright-level of the amount of light. If the signals thus binarized indicate bright areas at both ends of the potential shadow 3' and if it is determined their widths measured are within the range for the bright portions 2 created due to the diffraction of light, a judgment is made that the potential shadow 3' is the real shadow of an impurity.

With this arrangement, it is possible to pick out only those optical signals for the real shadows of impurities, while eliminating optical signals that indicate false shadows due to disturbance of optical signals resulting from the irregularity in the refractive index. In other words, it is possible to clearly distinguish impurities in the molten polymer from false shadows due to the irregularity in the refractive index of the polymer and thus to prevent errors in detection due to the irregularity in refractive index. Heretofore, such a clear distinction was difficult.

In order to the detect bright portions due to diffraction of light at both ends of the shadow of an impurity, optical signals for predetermined widths of areas at both ends of the potential shadow 3' may be integrated to see if the areas are actually bright portions caused due to the diffraction of light.

Before processing the optical signals in the above-described manner, their components which are slow to change or never change with the passage of time, which are known as a "fixed pattern", may be subtracted from the entire optical signal. Otherwise, the optical signal may be smoothed by filtering spatial high-frequency components in comparison with the shadow of an impurity.

The method of the present invention has the following advantages:

(1) Any impurities in molten polyethylene can be picked out by detecting its shadow irrespective of an the focal depth of the lens.

(2) Since a line sensor is used to detect the shadow of an impurity, it is not necessary to use a long a window for passing light. This eliminates the necessity of heating the molten polyethylene even though a glass portion is used.

(3) The diameter of the shadow corresponds to the maximum diameter of the impurity with respect to the direction in which light is emitted from the light source. Thus, the shadow is little influenced by the surface condition and the shape of the impurity, so that the optical signals have to be processed to a minimum degree. This means that the entire amount of molten polyethylene can be checked easily.

(4) The diameter of an impurity is calculated from the product of the width of the shadow and the intensity of light. Thus, the diameter can be measured with minimum error even if the shadow is blurred due to the interference of light. This also makes it possible to detect even a relatively small-diameter impurity.

(5) Since it is possible to distinguish between a disturbance of light due to an irregularity in refractive index and the real shadows of impurities, the former is never mistaken for the latter. Thus, the detection accuracy improves dramatically.

(6) Since it is possible to detect the position of an impurity, a device having a limited depth of field such as a camera having a conventional lens can be used to record or determine impurities.

Thus, the method according to the present invention is advantageously applicable when extruding an insulation coating on a CV cable or forming an extrusion-molded joint at a joint portion of the cable.

BRIEF DESCRIPTION OF THE DRAWINGS

Other features and objects of the present invention will become apparent from following description made with reference to the accompanying drawings, in which.

DESCRIPTION OF THE PREFERRED EMBODIMENTS

Figure 8:
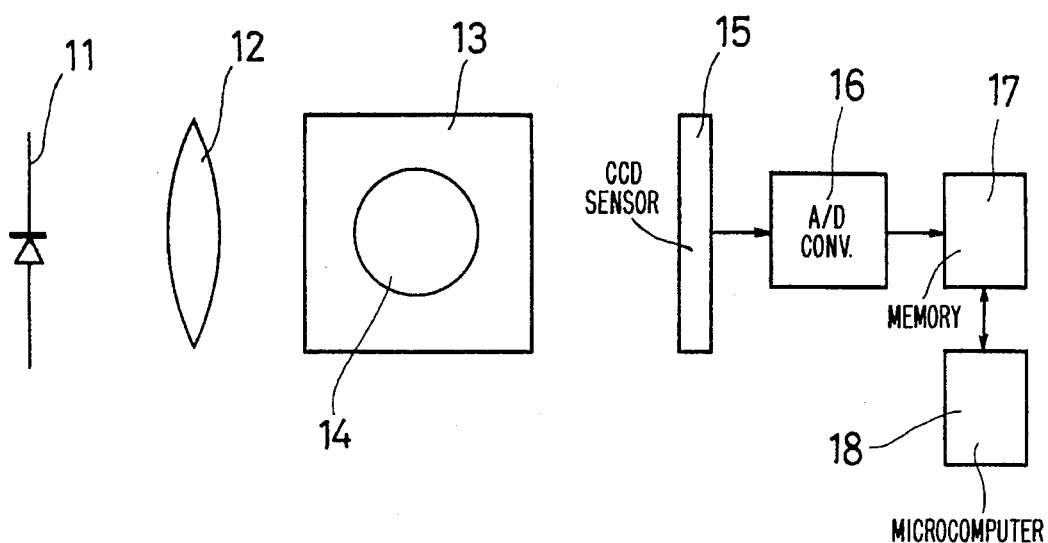
FIG. 8 is a view showing an arrangement used to carry out the method of the present invention.

FIG. 8 shows an arrangement for carrying out the method according to the present invention for distinguishing impurities in a molten resin.

As shown in the figure, the light emitted from an LED light source 11 is converted into parallel beams by means of a collimator lens 12, the parallel beams being passed through a molten polyethylene 14 flowing through a glass window 13. The beams passing through the polyethylene are converted into electrical signals by a CCD sensor 15, the signals being converted into digital signals by means of an A/D converter 16. The digital numerical signals thus obtained are stored in a memory 17 and are processed by a microcomputer 18.

The numerical signals stored in the memory are expressed by $a_1(t_k) \ldots a_n(t_k)$, where n is the number of pixels of the CCD sensor. E.g. $a_i(t_k)$ indicates the amount of light received by the i-th pixel at time $t_k$. In order to eliminate any components that are slow to change with time, from these numerical signals, the signals, $a_i(t_k), a_i(t_{k-1}), a_i(t_{k-2}), \ldots$ that represent the amounts of light received by each pixel at different time points are subjected to digital high-pass filtering. Numerical signals $b_1(t_k) \ldots b_n(t_k)$ (n is the number of pixels of CCD) which contain no components that are slow to change with time are obtained by subtracting the slow components $S_i(t_k)=((1/m)a_i \ (t_k)+(m-1)/m \ S_i(t_{k-1})$ (m×Δt is the time constant of the filter, m>0, Δt is the time interval between $t_k$ and $t_{k-1}$) from the numerical signals $a_i(t_k)$ (i.e. $b_i(t_k)=a_i(t_k)-S_i(t_k)$).

Further, in order to spatially smooth out the distribution of the amounts of light received, the signals $b_1(t_k) \ldots b_n(t_k)$ which represent the amounts of light received at a given point of time are subjected to digital low-pass filtering.

$$Ci(t_k) = \sum_{j=-e}^{e} H_j b_{i+j}(t_k)$$

(wherein $H_j$ determines the nature of the filter)

Through these filterings, spatially smoothed-out numerical signals $C_1(t_k) \ldots C_{n-e}(t_k)$, which contain no components that are slow to change with time, are obtained.

The signals $C_e(t_k) \ldots C_{n-e}(t_k)$ are compared with a threshold $a_{th}$ of the bright level. If each of these signals (which contain no slow components and are spatially smoothed) are brighter than the threshold, it is indicated by "1" and if not, by "0". Thus, binarized signals $D_e(t_k) \ldots D_{n-e}(t_k)$ are obtained.

Further, the signals $C_e(t_k) \ldots C_{n-e}(t_k)$ are compared with a threshold $\beta_{th}$ of the dark level. If each of the signals is darker than the threshold, it is indicated by "1" and if not, by "0". The thus binarized signals are represented by $E_e(t_k) \ldots E_{n-e}(t_k)$.

If, among the signals $E_e(t_k) \ldots E_{n-e}(t_k)$, dark-level signals are found continuously over a predetermined width, these parts are picked out as suspected shadows of impurities. Also, if bright-level signals are found continuously over a predetermined width among the signals $D_e(t_k) \ldots D_{n-e}(t_k)$, these parts are picked up as representing possible bright portions which appear at both ends of the shadow of an impurity due to diffraction of light. If such bright portions actually exist at both ends of the suspected shadows of impurities, such shadows are determined to be the real ones.

In this embodiment, a plurality of sets of the devices used in Embodiment 1 are used to further improve the accuracy of detection and size measurement of impurities.

Figure 1:
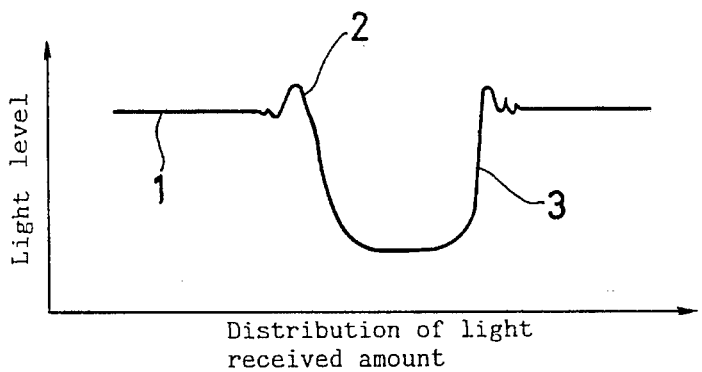
FIG. 1 is a view explaining the principle of the method according to the present invention.
Figure 2A:
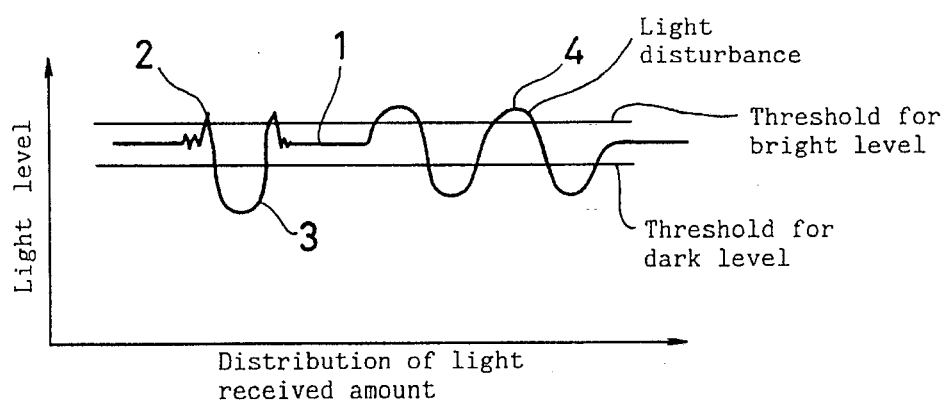
FIG. 2A is a graph showing the optical signals.
Figure 2B:
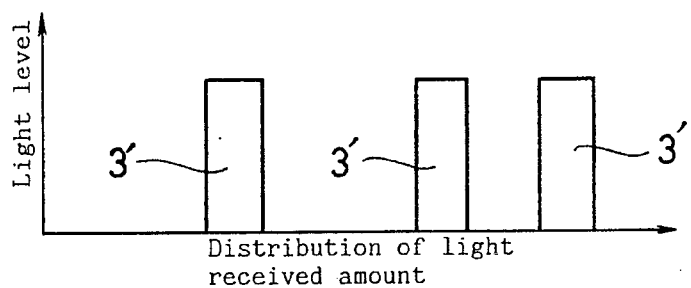
FIG. 2B is a view showing the outputs of a comparator for dark-level.
Figure 2C:
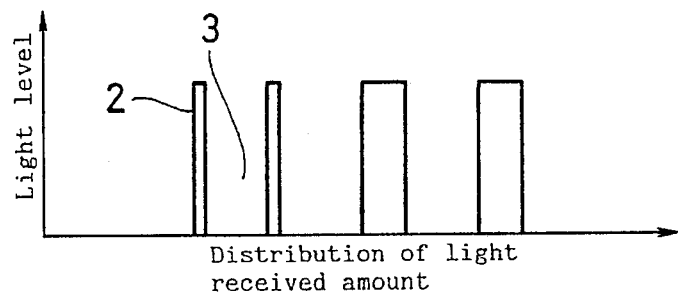
FIG. 2C is a view showing the outputs of a comparator for bright-level.
Figure 3A:
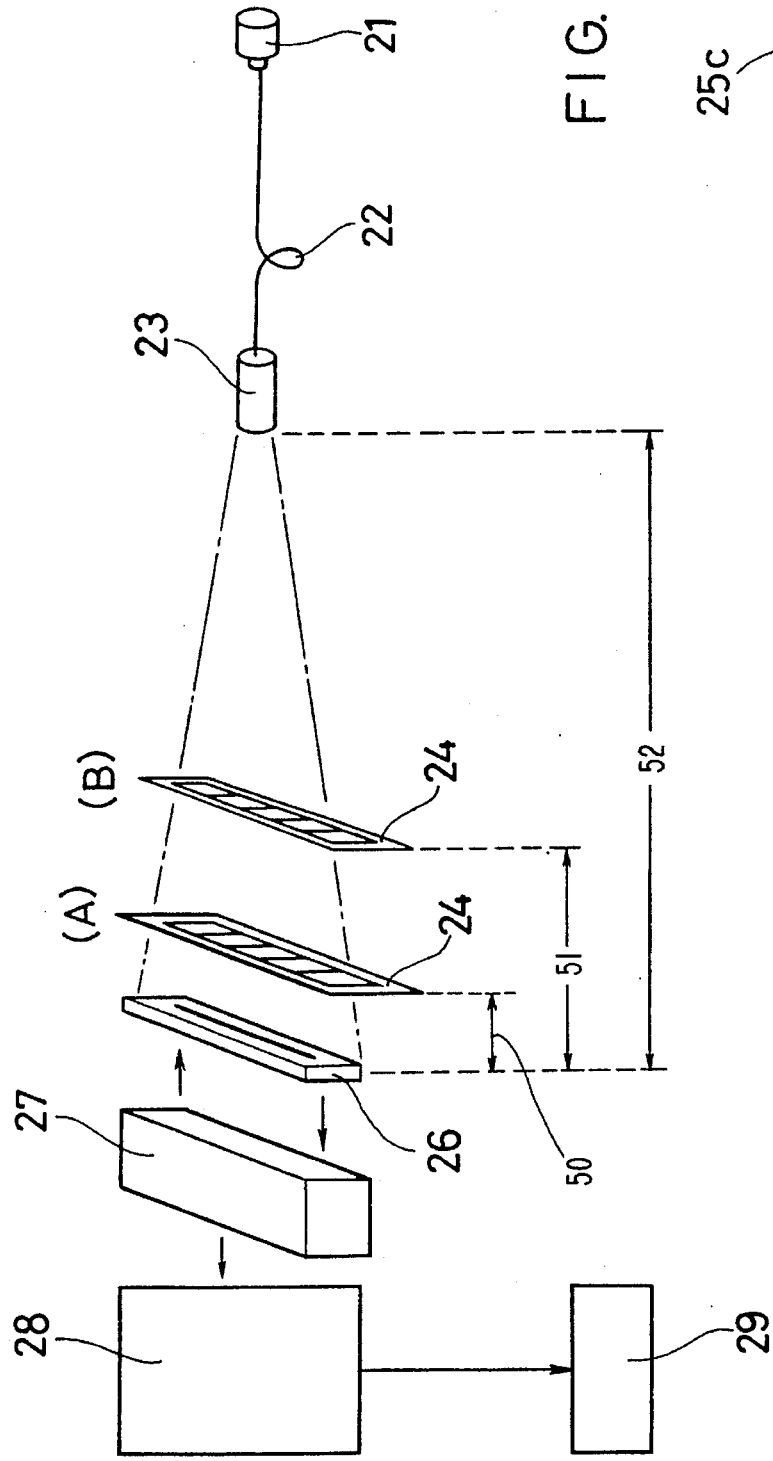
FIG. 3A is a schematic view showing how the experiments are conducted to measure the resolution, field of view and focal depth attainable with the method of the present invention.
Figure 3B:
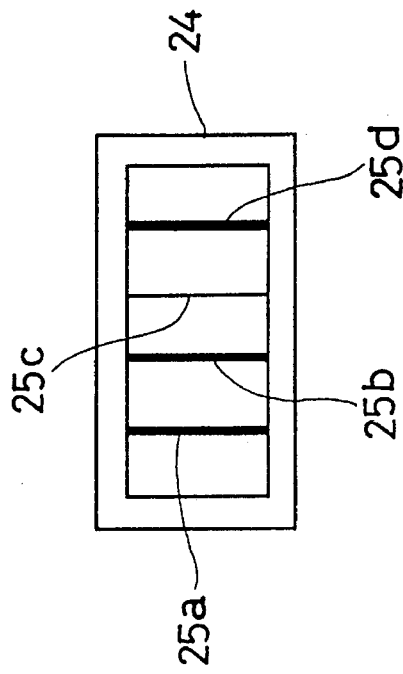
FIG. 3B is a view showing the specimen used in the experiments.
Figure 4A:
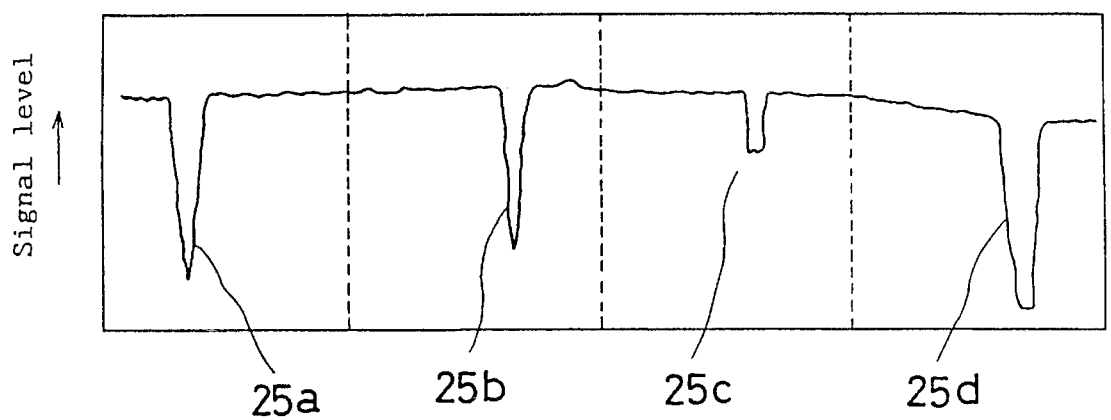
FIG. 4A is an image of the signal outputs of the CCD line sensor used in the experiment shown in FIG. 3A.
Figure 4B:
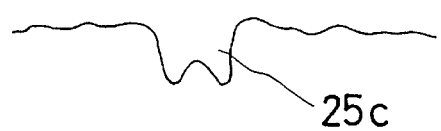
FIGS. 4B and 4C are enlarged views of the portions for 25c and 25d, respectively.
Figure 4C:
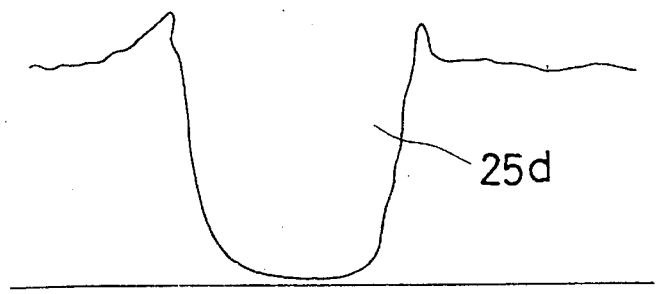
Figure 5A:
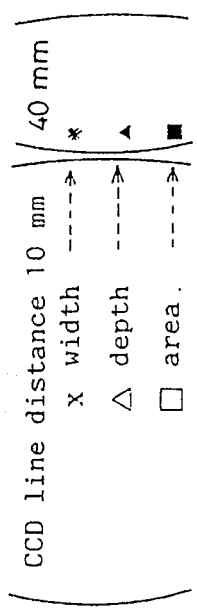
FIG. 5 is a graph showing the relationship between the diameters and shadows of impurities obtained in the experiments of FIG. 3A.
Figure 5B:
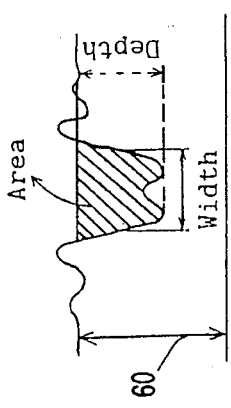
Figure 5C:
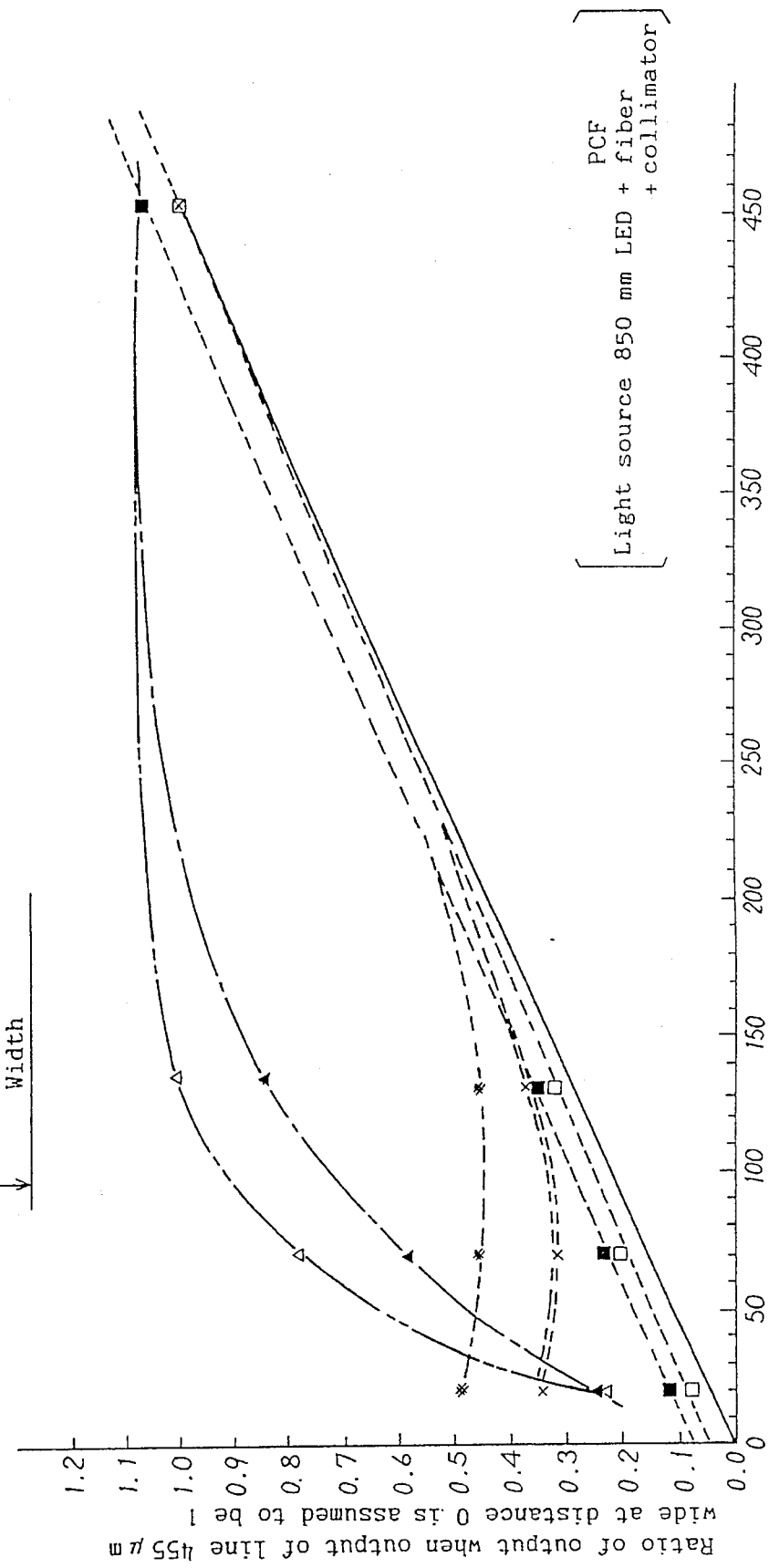
Figure 6:
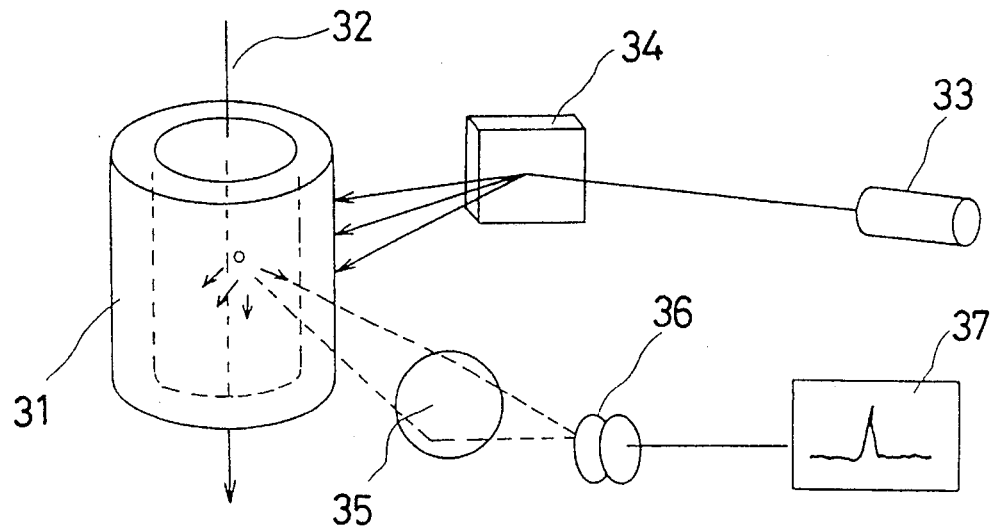
FIG. 6 is a view showing a conventional method of detecting impurities in molten polyethylene.
Figure 7:
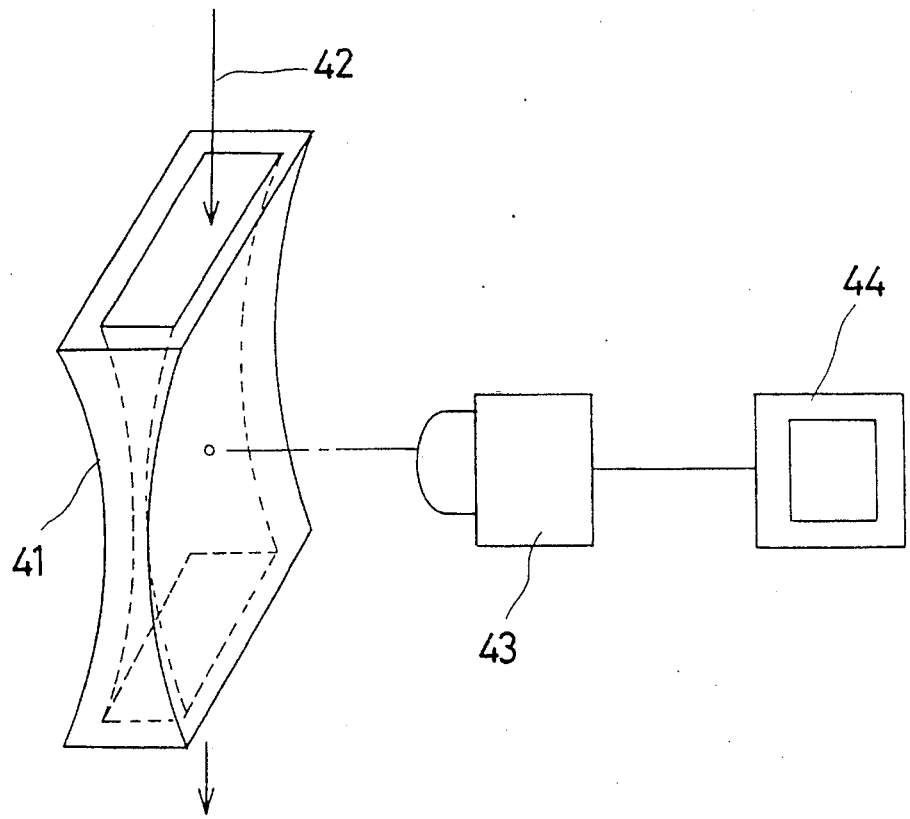
FIG. 7 is a view showing another conventional method.
Figure 9:
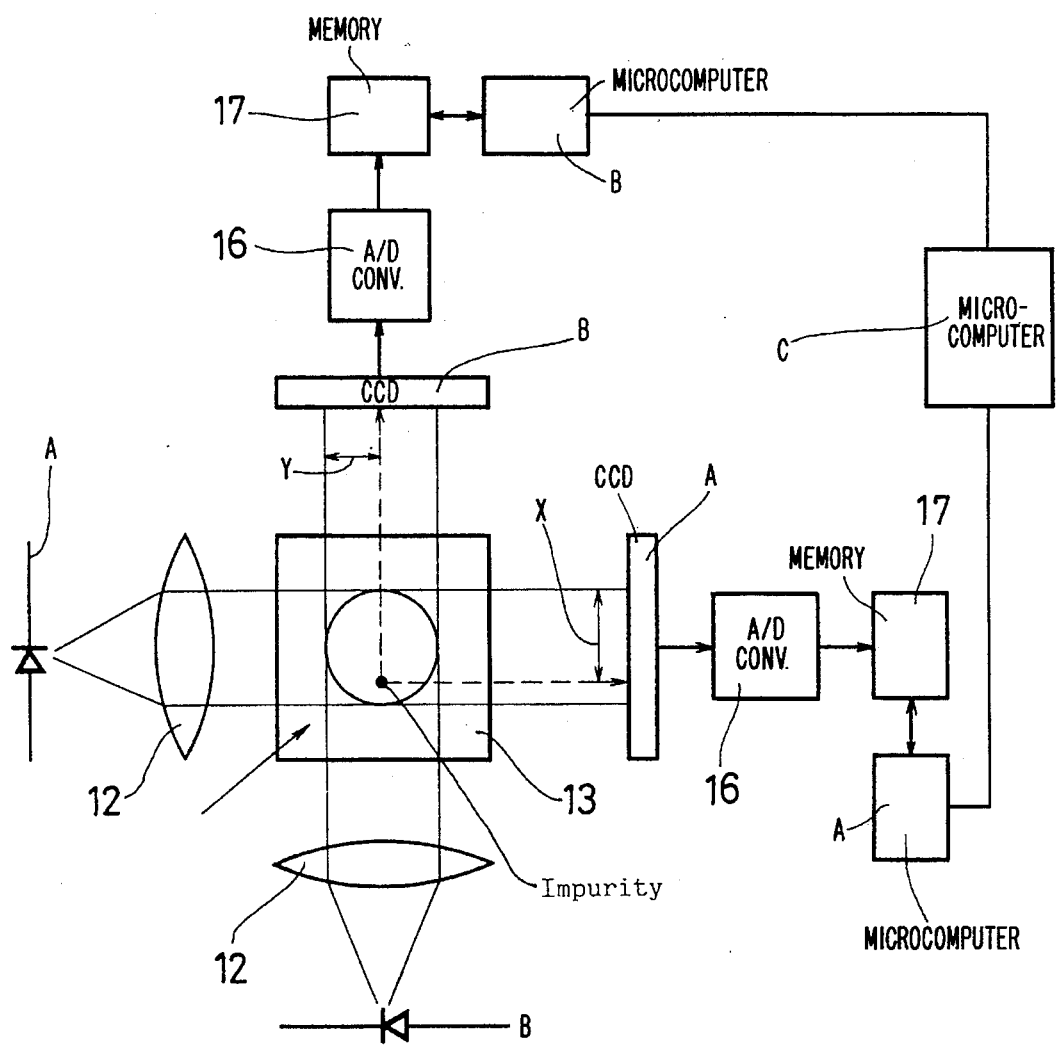
FIG. 9 is a view showing another arrangement which is a combination of two of the devices shown in FIG. 8.

FIG. 9 shows such an arrangement which uses two devices which are of the same type as the device used in Embodiment 1. The size of an impurity can be measured by the combination of a light source A and a CCD sensor A. As shown in FIG. 5, however, if the distance between the CCD sensor and an impurity changes by 30 mm, a measuring error of about 10 μm results for impurities having a diameter of 200 μm or less.

By providing two such devices so as to intersect with each other at a right angle, it is possible to determine the distance Y shown in the figure by the combination of a light source B and a CCD sensor B. For the device comprising the light source A and the CCD sensor A, the distance Y is the depth of subject. Thus, if the relationship between the area of shadow of an impurity and the distance Y is determined beforehand, it is possible to correct the results obtained in a microcomputer A according to the distance Y. In the arrangement of FIG. 9, the results obtained in microcomputers A and B are processed in the microcomputer C. Thus, the diameters of impurities can be measured more accurately.

By using a plurality of devices of the type used in Embodiment 1, the size of impurities can be detected with higher accuracy because their precise positions can be determined.

If the arrangement according to the present invention is used together with a conventional camera, it is possible to record images of impurities that show not only their size and positions but their colors.

Figure 10:
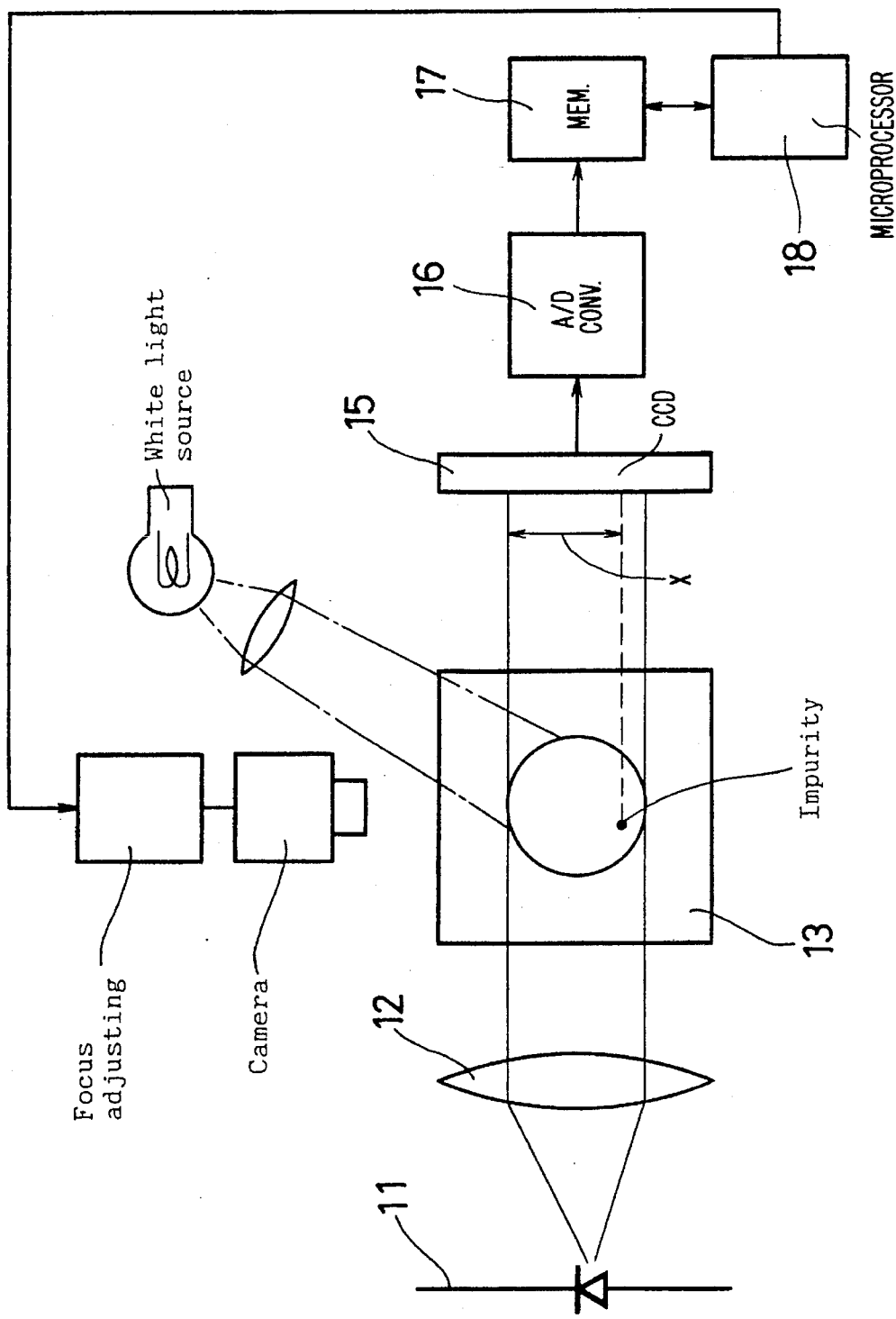
FIG. 10 is a view showing another arrangement using the device shown in FIG. 8 and a conventional device.

FIG. 10 shows another embodiment of the present invention, which comprises shadow detecting devices 11–18 and a focus-adjustable camera. The camera should be positioned downstream of the shape detecting devices with respect to the flow direction of resin.

With this arrangement, the distance x shown in the figure can be determined by the shadow detecting devices 11–18.

Thus, by focusing the camera according to the distance x, the image of an impurity can be detected vividly.

What is claimed is:

1. A method of detecting impurities in a molten resin comprising: passing the molten resin through a passage having a window through which light can pass; emitting light from a light source through said window and the molten resin flowing through said passage, sensing, by means of a sensor, shadows produced when the light from said light source is interrupted by an impurity contained in the molten resin, and measuring a size of the impurity from a product of a width of the shadow and an intensity of light from the shadow; wherein judgment is made that if optical signals obtained by detecting the light that has passed through the molten resin indicate that a bright area exists around a dark area, then said dark area is determine to be a shadow of an impurity.

2. A method as recited in claim 1, wherein the sensor is a line sensor.

3. A method as recited in claim 1, wherein the sensor is a CCD camera.

4. A method of detecting impurities in a molten resin comprising: providing at least two devices used in carrying out the method of detecting impurities in a molten resin by passing the molten resin through a passage having a window through which light can pass and emitting light from a light source through said window and the molten resin flowing through said passage and sensing, by means of a sensor, shadows produced when the light from said light source is interrupted by an impurity contained in the molten resin and measuring a size of the impurity from a width of the shadow and an intensity of light in the shadow, detecting the shadows of impurities contained in the molten resin by means of at least two sensors of said at least two devices to determine three-dimensional positions of the impurities, and correcting a size of the impurities according to the three-dimensional position thus obtained.

5. A method of detecting impurities in a molten resin comprising: combining a device used in carrying out the method of distinguishing impurities in a molten resin wherein shadows of impurities contained in the molten resin are detected by passing light from a light source through the molten resin, and wherein judgment is made that if optical signals obtained by detecting the light that has passed through the molten resin indicate that a bright area exists around a dark area, the said dark area is determined to be a shadow of an impurity with a focus-adjustable camera, detecting a position of the shadow of an impurity in the molten resin, and recording an image of the impurity by means of said camera after adjusting its focusing point according to said detected position of the shadow of the impurity.

6. A method of distinguishing impurities in a molten resin wherein shadows of impurities contained in the molten resin are detected by passing light from a light source through the molten resin, and wherein judgment is made that if optical signals obtained by detecting the light that has passed through the molten resin indicate that a bright area exists around a dark area, then said dark area is determined to be a shadow of an impurity.

7. A method, of distinguishing impurities in a molten resin wherein shadows of impurities contained in the molten resin are detected by passing light from a light source through the molten resin, and wherein judgment is made that if optical signals obtained by detecting the light that has passed through the molten resin indicate that a bright area exists around a dark area, the said dark area is determined to be a shadow of an impurity, further comprising: binarizing said optical signals by comparing said optical signals with a first threshold for a dark level; binarizing said optical signals by comparing said optical signals with a second threshold for a bright level; and determining that a dark area represented by the optical signals binarized according to the first threshold indicates a shadow of an impurity if there exists bright areas represented by the optical signals binarized according to the second threshold at both ends of said dark area.

* * * * *